United States Patent [19]

Gallenkamp

[11] Patent Number: 4,778,896
[45] Date of Patent: Oct. 18, 1988

[54] PROCESS FOR THE PREPARATION OF 5-CHLOROMETHYLPYRIDINES

[75] Inventor: Bernd Gallenkamp, Wuppertal, Fed. Rep. of Germany

[73] Assignee: Bayer Aktiengesellschaft, Leverkusen, Fed. Rep. of Germany

[21] Appl. No.: 86,418

[22] Filed: Aug. 17, 1987

[30] Foreign Application Priority Data

Sep. 4, 1986 [DE] Fed. Rep. of Germany ....... 3630046

[51] Int. Cl.$^4$ .......................................... C07D 213/26
[52] U.S. Cl. ................................... 546/304; 546/345; 546/346
[58] Field of Search ..................... 546/346, 304, 345

[56] References Cited

U.S. PATENT DOCUMENTS 3,123,608 3/1964 Mathes et al. ...................... 546/346
3,931,200 1/1976 Gulbenk ............................. 546/346
4,205,175 5/1980 Bowden et al. ..................... 546/346

FOREIGN PATENT DOCUMENTS 0163855 12/1985 European Pat. Off. ............ 546/346

OTHER PUBLICATIONS

J. W. Tilley, P. Levitan and R. W. Kierstead, *J. Het. Chem.*, 16, 333–337, (1979).
H. Fritz, C. D. Weis and T. Winkler, *Helv. Chim. Acta*, 59, 170–190, (1976).
W. Mathes and H. Schuly, *Angew. Chem.*, 235–240, (1963).
F. E. Ziegler and J. G. Sweeny, *J. Org. Chem.*, 34, 3545–3548, (1969).
Synthesis, Nr. 8, Aug. 1984, Seiten 676–679; G. R. Newkome et al: "Alpha-methyl functionalization of electron-poor heterocycles: free radical chlorination".

*Primary Examiner*—Alan L. Rotman
*Assistant Examiner*—Robert C. Whittenbaugh
*Attorney, Agent, or Firm*—Sprung Horn Kramer & Woods

[57] ABSTRACT

A process for the preparation of 5-chloromethylpyridines of the formula (I)

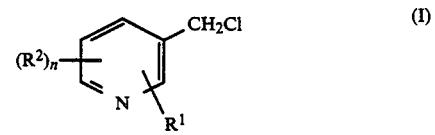

in which
$R^1$ represents chlorine or nitro,
$R^2$ represents chlorine, and
n represents the number 0 to 1, comprising chlorinating 5-methylpyridine of the formula (II)

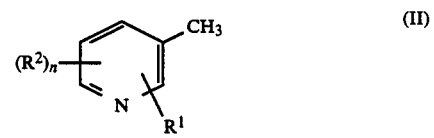

in which $R^1$, $R^2$ and n have the abovementioned meanings, at temperatures between 0° C. and 100° C., if appropriate in the presence of acid acceptors and if appropriate in the presence of inert diluents.

7 Claims, No Drawings

PROCESS FOR THE PREPARATION OF 5-CHLOROMETHYLPYRIDINES

The present invention relates to a new process for the preparation of 5-chloromethylpyridines, which can be used, for example, as intermediates for the preparation of insecticides.

It is already known that 5-chloromethylpyridines can be obtained by reacting 5-hydroxymethylpyridines with chlorinating agents, such as, for example, thionyl chloride (cf. EP-OS (European Published Specification) No. 163,855 and J. Het. Chem. 16, 333 (1979)). This process has the disadvantage that many reaction stages are necessary for the preparation of 5-chloromethylpyridines.

It is furthermore known that direct chlorination of the methyl group of 3-methylpyridines is not possible (cf. Helv. Chim. Acta 59, 179 ff (1976) and Angew. Chem. 1963, 236 ff).

It has now been found that 5-chloromethylpyridines of the general formula (I)

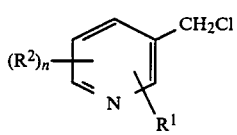

in which
R1 represents chlorine or nitro,
R2 represents chlorine, and
n represents the number 0 or 1,
are obtained when 5-methylpyridines of the formula (II)

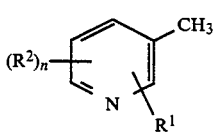

in which R$^1$, R$^2$ and n have the abovementioned meanings, are chlorinated at temperatures between 0° C. and 100° C., if appropriate in the presence of acid acceptors and if appropriate in the presence of inert diluents.

Surprisingly, the process according to the invention can successfully be used to prepare 5-chloromethylpyridines in a simple fashion and at low expense by direct chlorination of corresponding 5-methylpyridines. According to the state of the art, 4 complicated reaction stages are necessary for the preparation of 5-chloromethylpyridines:

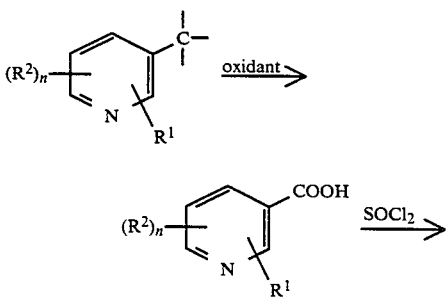

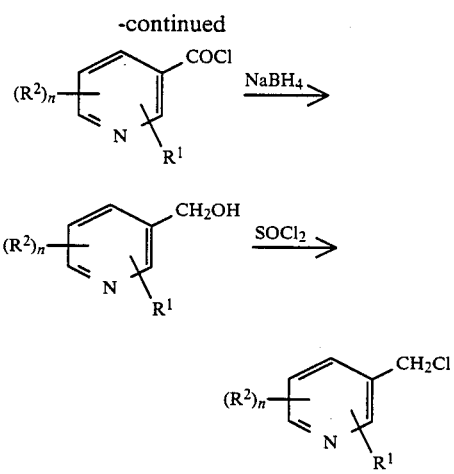

(cf. J. Org. Chem. 34, 3545 (1969) and J. Het. Chem. 16, 333 (1979)). This problematic reaction sequence can now be avoided in a surprisingly simple fashion.

The process according to the invention is preferred for preparing the following compounds of the formula (I): 2-chloro-, 2,3-dichloro-, 4-chloro , 2,4-dichloro- and 2-nitro-5-chloromethylpyridine.

The process according to the invention is particularly preferred for preparing the following compound of the formula (I): 2-chloro-5-chloromethylpyridine.

If 2-chloro-5-methyl-pyridine and elemental chlorine are used as starting materials in the process according to the invention, the reaction can be represented by the following equation:

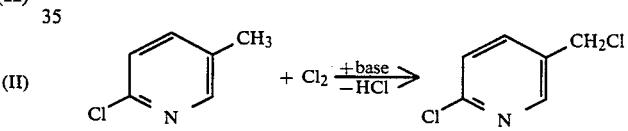

Formula (II) provides a general definition of the 5-methylpyridines to be used as starting materials for the process according to the invention. In this formula, R$^1$ and R$^2$ preferably represent those radicals which are given above as being preferred or as being particularly preferred in the context of the definition of the substituents in the formula (I).

Examples of compounds of the formula (II) which may be mentioned are: 2-chloro-, 2,3-dichloro-, 4-chloro-, 2,4-dichloro- and 2-nitro-5-methylpyridine.

The compounds of the formula (II) are known or can be prepared in an analogous fashion by known processes.

The process, according to the invention, for the preparation of compounds of the formula (I) is preferably carried out using diluents. Suitable diluents in this process are virtually all inert organic solvents. These include, preferably, aliphatic, optionally halogenated hydrocarbons, such as methylene chloride, ethylene chloride, chloroform and carbon tetrachloride, ethers, such as diethyl and dibutyl ether, methyl tert.-butyl ether, glycol dimethyl ether and diglycol dimethyl ether, tetrahydrofuran and dioxane.

The process according to the invention is preferably carried out in the presence of acid acceptors. Acid acceptors which can be employed in the process according to the invention are all acid-binding agents which can conventionally be used for such reactions Preferably suitable are alkali metal carbonates, such as sodium carbonate and potassium carbonate, furthermore aliphatic, aromatic or heterocyclic amines, for example triethylamine, trimethylamine, dimethylaniline, dimethylbenzylamine, pyridine, 1,5-diazabicyclo-[4,3,0]-non-5-ene (DBN), 1,8-diazabicyclo-[5,4,0]-undec-7-ene (DBU) and 1,4-diazabicyclo-[2,2,2]-octane (DABCO).

The reaction temperatures can be varied within a relatively wide range in the process according to the invention. In general, the process is carried out at temperatures between 0° C. and 100° C. , preferably at temperatures between 40° C. and 80° C. . The process according to the invention is generally carried out under atmospheric pressure.

To carry out the process according to the invention in a preferred manner, elemental chlorine is passed through a mixture of starting material of the formula (II), acid acceptor and diluent, and the reaction mixture is stirred for several hours at the temperature necessary in each case (preferably in the range 40° to 80° C. ). Work-up is effected by generally conventional methods.

The 5-chloromethylpyridines to be prepared by the process according to the invention can be employed, for example, as intermediates for the preparation of nitromethylene derivatives which are effective as insecticides (cf. EP-A No. 163,855).

In this connection, the following further processing equation may be shown as an example:

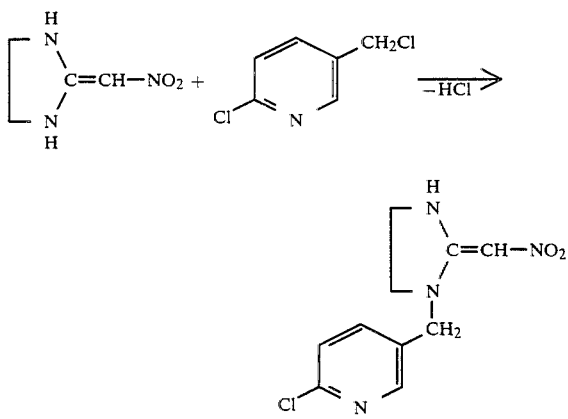

PREPARATION EXAMPLE

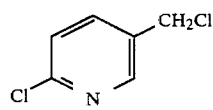

Elemental chlorine is passed through a solution of 2.54 g (0.02 mol) of 2-chloro-5-methylpyridine and 4 g (0.0265 mol) of sodium carbonate in 10 ml of carbon tetrachloride at 60° C. . The course of the reaction is followed by gas chromatography. After 10 hours, the reaction mixture is cooled and concentrated.

2.1 g (65% of theory) of 2-chloro-5-chloromethylpyridine are obtained. The structure is confirmed by $^1$H NMR spectra.

$^1$NMR (CDCl$_3$): δ=8.4 (d, 1H, —CH—N=), 7.73 (dd,1H,

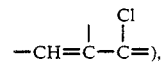

7.35 (d, 1H,

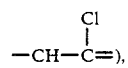

4.57 (s, 2H, —CH$_2$) ppm.

It will be appreciated that the instant specification and claims are set forth by way of illustration and not limitation, and that various modifications and changes may be made without departing from the spirit and scope of the present invention.

What is claimed is:

1. A process for the preparation of a 5-chloromethylpyridine of the formula (I)

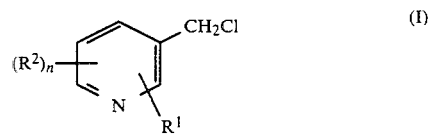

in which
R$^1$ represents chlorine or nitro,
R$^2$ represents chlorine, and
n represents the number 0 or 1, comprising chlorinating a 5-methylpyridine of the formula

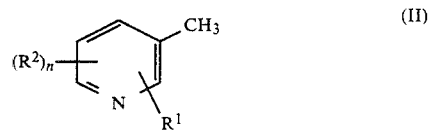

in which
R$^1$, R$^2$ and n have the abovementioned meanings, at temperatures between 0° C. and 100° C. in the presence of an acid acceptor selected from the group consisting of an alkali metal carbonate, an aliphatic amine, an aromatic amine, and a heterocyclic amine and in the presence of an inert diluent, the resultant reaction mixture being stirred for several hours.

2. A process according to claim 1, wherein the acid acceptor is selected from the group consisting of sodium carbonate; potassium carbonate; triethylamine; trimethylamine; dimethylaniline; dimethylbenzylamide; pyridine; 1,5-diazabicyclo-[4,3,0]-non-5-ene; 1,8-diazabicyclo-[5,4,0]-undec-7-ene and 1,4-diazabicyclo-[2,2,2]-octane.

3. A process according to claim 1, wherein the inert diluent is selected from the group consisting of an aliphatic hydrocarbon halogenated aliphatic hydrocarbon and an ether.

4. A process according to claim 3, wherein the inert diluent is a halogenated aliphatic hydrocarbon.

5. A process according to claim 1, wherein the diluent is selected from the group consisting of methylene chloride, ethylene chloride, chloroform, carbon tetrachloride, diethyl ether, dibutyl ether, methyl tert.-butyl ether, glycol dimethyl ether, diglycol dimethyl ether, tetrahydrofuran and dioxane.

6. A process according to claim 1, wherein the chlorination is carried out at temperatures between 40° C. and 80° C.

7. A process according to claim 1, wherein the 5-chloromethylpyridine is 2-chloro-5chloromethylpyridine.

* * * * *

UNITED STATES PATENT AND TRADEMARK OFFICE
CERTIFICATE OF CORRECTION

PATENT NO. : 4,778,896

DATED : October 18, 1988

INVENTOR(S) : Bernd Gallenkamp

It is certified that error appears in the above-identified patent and that said Letters Patent is hereby corrected as shown below:

Col. 3, line 67      Delete "$^1$NMR" and substitute --$^1$H NMR--

Col. 4, line 66      After "5" insert -- - --

Signed and Sealed this

Twentieth Day of June, 1989

Attest:

DONALD J. QUIGG

Attesting Officer      Commissioner of Patents and Trademarks